United States Patent [19]

Matsumoto et al.

[11] Patent Number: 4,722,934
[45] Date of Patent: Feb. 2, 1988

[54] THIADIAZOLE DERIVATIVE AND INSECTICIDAL AND MITICIDAL COMPOSITION CONTAINING THE SAME AS AN ACTIVE INGREDIENT

[75] Inventors: Susumu Matsumoto; Shigeru Suzuki, both of Yokohama; Hiroki Ohta, Kokubunji; Yoshiaki Higashino; Toshiki Fukuchi, both of Yokohama, all of Japan

[73] Assignee: Mitsubishi Chemical Industries Limited, Tokyo, Japan

[21] Appl. No.: 26,198

[22] Filed: Mar. 16, 1987

[30] Foreign Application Priority Data

Mar. 25, 1986 [JP] Japan .................... 61-66858

[51] Int. Cl.$^4$ .................... C07D 285/12; A01N 43/82
[52] U.S. Cl. .................... 514/363; 548/136; 548/138
[58] Field of Search .................. 548/136, 138; 514/363

Primary Examiner—Robert Gerstl
Attorney, Agent, or Firm—Oblon, Fisher, Spivak, McClelland & Maier

[57] ABSTRACT

The present invention relates to a thiadiazole derivative of the following general formula (I) and an insecticidal and miticidal composition containing the same as an active ingredient:

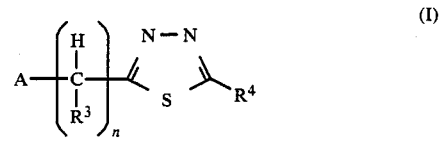

wherein A represents a group of the formula

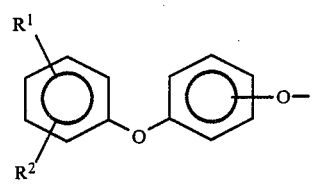

$R^1$ and $R^2$ independently represent a hydrogen atom, a halogen atom, a lower alkyl group, a trifluoromethyl group, a cyano group or a nitro group or jointly represent a methylenedioxy group, $R^3$ represents a hydrogen atom or a lower alkyl group, $R^4$ represents a lower alkyl group, a lower alkoxy group, a lower alkylthio group, a monoalkylamino group having a lower alkyl group or a dialkylamino group having lower alkyl group, and n is an integer of from 1 through 3.

14 Claims, No Drawings

THIADIAZOLE DERIVATIVE AND INSECTICIDAL AND MITICIDAL COMPOSITION CONTAINING THE SAME AS AN ACTIVE INGREDIENT

The present invention relates to a novel thiadiazole derivative and an insecticidal and miticidal composition containing the same as an active ingredient.

(N)-thiadiazorylbenzamide derivative is disclosed in U.S. Pat. No. 4,141,984 and U.S. Pat. No. 4,271,166 as a heterocyclic compound having a thiadiazole ring among heterocyclic derivatives having an insecticidal activity. However, the thiadiazole derivative which has a phenoxyphenoxyalkylene substituent is not known.

On the other hand, 1,2,4-triazoline-5-one derivative or 1,3,4-oxadiazoline-5-one derivative is disclosed in Japanese Unexamined Patent Publication No. 215675/85 as a compound having a phenoxyphenoxyalkylene substituent among heterocyclic derivatives having an insecticidal activity. Due to the modification in the chemical structure of the compound, however, the presence or absence, extent, etc. of the insecticidal activity can not be estimated at all.

In recent years, it has become difficult to control pest insects by conventional insecticides because the pest insects have acquired resistance through the extensive use of the insecticides for many years. For example, against representative insecticides, organic phosphorus agents and carbamate agents, pest insects having resistance to them have come to breed, and the control of them is getting difficult. Further, the development of resistance to synthetic pyrethloid-based insecticides has been reported, the insecticides having come into the limelight in recent years. Meanwhile, some of the organic phosphorus agents or carbamate agents are high in toxicity and others disturb an ecosystem due to residual toxicity, assuming a very serious situation. Accordingly, the development of a novel insecticide is hoped for which shows an excellent control effect even on pest insects having resistance to the conventional insecticides and is low in toxicity and residual toxicity.

This invention provides a novel thiadiazole derivative having an excellent insecticidal and miticidal activity.

The gist of the invention lies in a thiadiazole derivative of the following general formula (I) and an insecticidal and miticidal composition containing the same for its active ingredient;

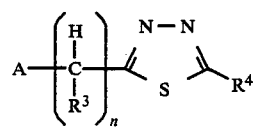

wherein A represents a group of the formula

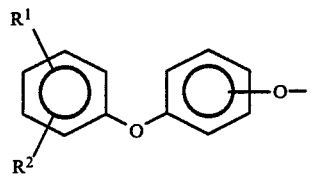

$R^1$ and $R^2$ independently represent a hydrogen atom, a halogen atom, a lower alkyl group, a trifluoromethyl group, a cyano group or a nitro group or jointly represent a methylenedioxy group, $R^3$ represents a hydrogen atom or a lower alkyl group, $R^4$ represents a lower alkyl group, a lower alkoxy group, a lower alkylthio group, a monoalkylamino group having a lower alkyl group or a dialkylamino group having lower alkyl group, and n is an integer of from 1 through 3.

The invention will be described in detail. In the general formula (I), A represents a group of the formula

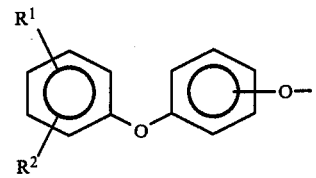

$R^1$ and $R^2$ independently represent a hydrogen atom, a halogen atom, a $C_1$ to $C_4$ lower alkyl group, a trifluoromethyl group, a cyano group or a nitro group or jointly represent a methylenedioxy group, $R^3$ represents a hydrogen atom or a $C_1$ to $C_4$ lower alkyl group, $R^4$ represents a $C_1$ to $C_4$ lower alkyl group, a $C_1$ to $C_4$ lower alkoxy group, a $C_1$ to $C_4$ lower alkylthio group, a monoalkylamino group having a $C_1$ to $C_4$ alkyl group or a dialkylamino group having $C_1$ to $C_4$ alkyl group, and n is an integer of from 1 through 3.

Preferably from a point of insecticidal and miticidal activity, A represents a group of the formula

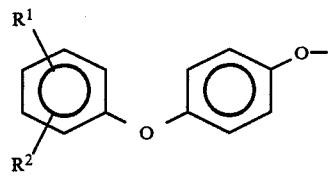

$R^1$ and $R^2$ independently represent a hydrogen atom, a halogen atom, a $C_1$ to $C_4$ lower alkyl group, a trifluoromethyl group or a cyano group or jointly represent a methylenedioxy group, $R^3$ represents a hydrogen atom or a $C_1$ to $C_4$ lower alkyl group, $R^4$ represents a $C_1$ to $C_3$ lower alkyl group, a $C_1$ to $C_4$ lower alkoxy group, a $C_1$ to $C_3$ lower alkylthio group, a monoalkylamino group having a $C_1$ to $C_2$ alkyl group or a dialkylamino group having $C_1$ to $C_2$ alkyl group, and n is an integer of from 1 through 3.

More preferably, A represents a group of the formula

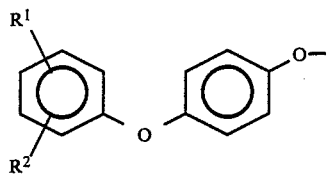

$R^1$ and $R^2$ independently represent a hydrogen atom, a halogen atom, a trifluoromethyl group or a cyano group, $R^3$ represents a $C_1$ to $C_3$ lower alkyl group, $R^4$ repreents a $C_1$ to $C_3$ lower alkoxy group or a $C_1$ to $C_3$ lower alkylthio group, and n is 1.

Especially preferably, A represents a group of the formula

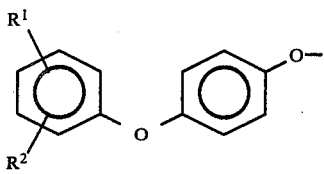

$R^1$ and $R^2$ independently represent a hydrogen atom, a chlorine atom, a bromine atom, a trifluoromethyl group or a cyano group, $R^3$ represents a methyl group, $R^4$ represents a $C_1$ to $C_3$ lower alkoxy group, and n is 1.

Further, a compound of the general formula (I) wherein either of $R^1$ and $R^2$ is a halogen atom, a trifluoromethyl group or a cyano group by which the 4-position is substituted in the substituent A, a group of the formula

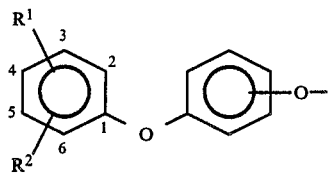

is generally preferable irrespective of the kinds of $R^3$ and $R^4$.

The most preferable is a compound of the general formula (I) wherein A represents a group of the formula

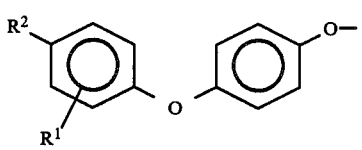

$R^1$ is a hydrogen atom, $R^2$ is a trifluoromethyl group, $R^3$ is a methyl group, $R^4$ is a $C_1$ to $C_3$ lower alkoxy group, and n is 1.

A thiadiazole derivative of the general formula (I) is obtained by the cyclization and condensation of a hydrazine derivative of the formula (II) in the presence of a dehydrating agent

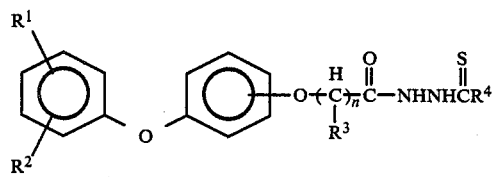

wherein $R^1$, $R^2$, $R^3$, $R^4$ and n have the same meaning as defined above. Examples of the dehydrating agent used include concentrated sulfuric acid, phosphorus pentaoxide, phosphorus pentasulfide, polyphosphoric acid, acetic anhydride, methanesulfonic acid, etc. The reaction is usually carried out without a solvent. According to circumstances, it may be carried out in inert solvents: aromatic hydrocarbons such as benzene, toluene, xylene, etc.; halogenated hydrocarbons such as methylene chloride, chloroform, 1,1,2,2-tetrachlorethane, etc.; or ethers such as ether, tetrahydrofuran, dioxane, etc. The reaction temperature is usually about $-10$ to 200° C. depending on the kind of the dehydrating agent used.

The compound of the general formula (II) is synthesized according to the description in U.S. Pat. No. 4,526,609, for example, from an acid chloride and a hydrazine derivative which behave as follows:

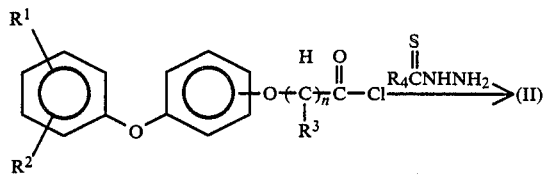

wherein $R^1$, $R^2$, $R^3$, $R^4$ and n have the same meaning as defined above.

In the case where $R^4$ represents an alkylthio group in the general formula (I), the thiadiazole derivative of the general formula (I) can be produced by the following method:

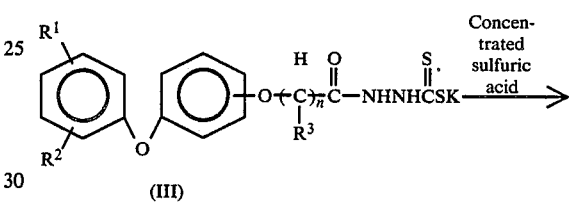

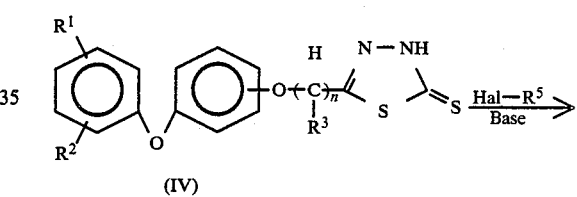

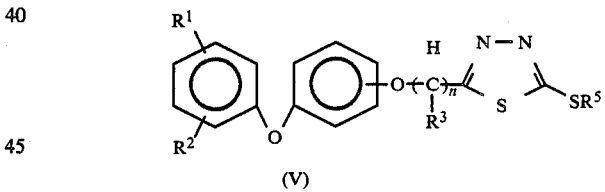

wherein $R^1$, $R^2$, $R^3$ and n have the same meaning as defined above, $R^5$ represents a lower alkyl group, and Hal represents a halogen atom.

In the above reaction, the thiadiazolethione derivative of the general formula (IV) is obtained by the cyclization and condensation of the hydrazine derivative of the general formula (III) in concentrated sulfuric acid at about $-10°$ to 0° C. The thiadiazole derivative of the general formula (V) is obtained by the reaction of the thiadiazolethione derivative of the general formula (IV) with a halogenated alkyl in the presence of a base. Examples of the base favorably used include inorganic bases such as alkali metal hydroxides (sodium hydroxide, potassium hydroxide, etc.) and alkali metal carbonates (sodium carbonate, potassium carbonate, etc.) or organic bases such a pyridine, triethylamine, etc. The reaction is usually carried out at 0° to 150° C., preferably at 20° to 100° C., in solvents: ketones such as acetone, methyl ethyl ketone, etc.; aromatic hydrocarbons such as benzene, toluene, etc.; and polar solvent such as tetrahydrofuran, acetonitrile, N,N-dimethylformamide, dimethyl sulfoxide, etc.

The compound of the general formula (III) is obtained by the reaction of a hydrazine derivative of the formula

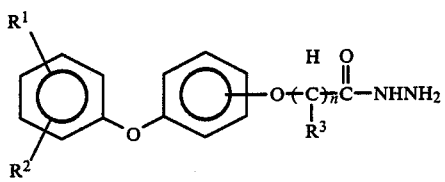

wherein $R^1$, $R^2$, $R^3$ and n have the same meaning as defined above, with carbon disulfide and pottasium hydroxide.

The present compound of the general formula (I) can also be produced by the following method. Namely, it can be obtained by the reaction of a diphenyl ether derivative of the formula (VI)

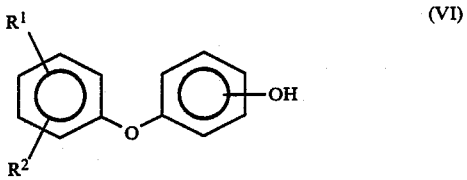

wherein $R^1$ and $R^2$ have the same meaning as defined above with a thiadiazole derivative of the formula (VII)

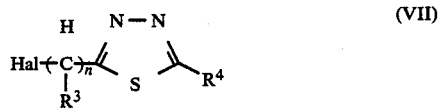

wherein $R^3$, $R^4$ and n have the same meaning as defined above and Hal represents a halogen atom, in the presence of a base.

Examples of the base favorably used in the above reaction include inorganic bases such as alkali metal hydroxides (sodium hydroxide, potassium hydroxide, etc.) and alkali metal carbonates (sodium carbonate, potassium carbonate, etc.) or organic bases such as pyridine, triethylamine, etc. The reaction is usually carried out at 0° to 150° C., preferably at 20° to 100° C., in solvents: ketones such as acetone, methyl ethyl ketone, etc.; aromatic hydrocarbons such as benzene, toluene, etc.; polar solvent such as tetrahydrofuran, acetonitrile, N,N-dimethylformamide, dimethyl sulfoxide, etc.

The compound of the general formula (I) has a great control activity against the following insects such as Coleoptera, Lepidoptera, Hemiptera, Diptera, etc. and eggs and larvae of Acarina. It goes without saying that the insects, eggs and larvae are not limited to them.

1 Hemiptera:
planthoppers such as white-backed planthopper (*Sogatella furcifera*), brown planthopper (*Nilaparvata lugens*), smaller brown planthopper (*Leoderphax striatellus*), etc. leafhoppers such as green rice leafhopper (*Nephotettix cincticeps*), green leafhopper (*Cicadella viridis*), etc. aphids such as green peach aphid (*Myzus percicae*), etc.

2. Lepidoptera:
common cutworm (*Spodoptera litura*), rice stem borer (*Chilo suppressalis*), rice leafroller (*Cnaphalocrocis medinalis*), etc.

3. Coleoptera:
adzuki bean weevil (*Callosobruchus maculatus*), etc.

4. Diptera:
housefly (*Musca domestica*), yellowfever mosquito (*Aedes aegypti*), northern house mosquito (*Culex pipiens pallens*), etc.

5. Acarina:
two-spotted spider mite (*Tetranychus urticae*), carmine spider mite (*Tetranychus cinnabarinus*), citrus red mite (*Panonychus citri*), etc.

When the present compound of the general formula (I) is used as an insecticide or a miticidal agent, it may be used alone. Usually, however, it is prepared into the form of emulsion, dust, wettable powder, liquid or the like using appropriate adjuvants and used as such or after dilution, similarly to conventional agricultural chemicals. As the adjuvant is used an ordinary one which is used for the preparation of insecticides. Examples of the adjuvant include: solid carriers such as talc, kaolin, diatomaceous earth, clay, starch, etc.; solvents such as water, hydrocarbons (cyclohexane, benzene, xylene, toluene, etc.), halogenated hydrocarbons (chlorobenzene, etc.), ethers, amides (dimethylformamide, etc.), ketones, alcohols and nitriles (acetonitrile, etc.); and other known surfactants such as emulsifiers, dispersants, etc.

If desired, the compound of the invention may be used in admixture or in combination with other insecticides, miticidal agents, germicides, insect's growth regulating substances, plant's growth regulating substances, etc.

The concentration of the active ingredient in a prepared insecticidal and miticidal composition is not particularly restricted. Usually, 0.5 to 20% by weight, preferably 1 to 10% by weight, of the active ingredient is contained in a dust; 1 to 90% by weight, preferably 10 to 80% by weight, in a wettable powder; and 1 to 90% by weight, preferably 10 to 40% by weight, in an emulsion.

When the compound of the formula (I) is used as an insecticide, it is usually used in the active ingredient concentration range of 5 to 1000 ppm, preferably 10 to 500 ppm.

Hereinafter, the invention will be more fully described in conjunction with the following production examples, preparation examples and test examples of the compounds of the invention, which are not to be construed as limiting the scope of the invention.

EXAMPLE 1

2-ethoxy-5-[1-[4-(4-chlorophenoxy)phenoxy]-ethyl]-1,3,4-thiadiazole

To 10 ml of concentrated sulfuric acid cooled to $-5°$ C. was added, with stirring, 2.0 g of 3-[2-[4-(4-chlorophenoxy)phenoxy]-propionyl]-thiocarbazic acid-O-ethyl ester gradually. After stirring at the same temperature for 10 minutes, the reaction mixture was poured over 100 g of ice followed by extracting with ethyl acetate. The resulting ethyl acetate layer was washed with water, dried over anhydrous sodium sulfate, and concentrated. The residue was purified by chromatography on silica gel to obtain 1.0 g of the compound No. 7 described in Table 1.

EXAMPLE 2

2-ethoxy-5-[1-[4-(4-trifluoromethylphenoxy)phenoxy]-ethyl]-1,3,4-thiadiazole

To 10 ml of concentrated sulfuric acid cooled to −5° C. was added, with stirring, 2.0 g of 3-[2-[4-(4-trifluoromethylphenoxy)phenoxy]-propionyl]-thiocarbazic acid-O-ethyl ester gradually. After stirring at the same temperature for 10 minutes, the reaction mixture was poured over 100 g of ice followed by extracting with ethyl acetate. The resulting ethyl acetate layer was washed with water, dried over anhydrous sodium sulfate, and concentrated. The residue was purified by chromatography on silica gel to obtain 1.1 g of the compound No. 5 described in Table 1.

EXAMPLE 3

2-[1-[4-(4-trifluoromethylphenoxy)phenoxy]-ethyl]-5-methylthio-1,3,4-thiadiazole To 40 ml of concentrated sulfuric acid cooled to −5° C. was added, with stirring, 4.0 g of 3-[2-[4-(4-trifluoromethylphenoxy)phenoxy]-propionyl]-potassium dithiocarbazate gradually. After stirring at the same temperature for 30 minutes, the reaction mixture was poured over 200 g of ice. The crystals precipitated were filtered off, washed with water and dried to obtain 2.2 g of 5-[1-[4-(4-trifluoromethylphenoxy)phenoxy]-ethyl]-1,3,4-thiadiazole-2-thione. This product was dissolved in 20 ml of acetone followed by adding 1.2 g of anhydrous potassium carbonate and 1.7 g of methyl iodide and refluxing with heating for 1 hour. After cooling, insoluble salts were filtered off, and acetone was distilled off under reduced pressure. The residue was dissolved in ethyl acetate followed by washing with water for two times, and the resulting ethyl acetate layer was dried over anhydrous sodium sulfate. Ethyl acetate was distilled off under reduced pressure, and the residue was purified by chromatography on silica gel to obtain 1.8 g of the compound No. 6 described in Table 1.

EXAMPLE 4

2-ethoxy-5-[(4-phenoxy)phenoxy]-methyl-1,3,4-thiadiazole 0.76 g of 4-phenoxy phenol was dissolved in 10 ml of acetone followed by adding 0.6 g of anhydrous potassium carbonate and 1.0 g of 2-bromomethyl-5-ethoxy-1,3,4-thiadiazole. The resulting mixture was refluxed with stirring and heated for 2 hours. After cooling, 100 ml of ethyl acetate was added followed by washing with water for two times, and the resulting ethyl acetate layer was dried over anhydrous magnesium sulfate. Ethyl acetate was distilled over under reduced pressure, and the residue was purified by chromatography on silica gel to obtain 1.0 g of the compound No. 1 described in Table 1.

EXAMPLE 5

2-ethoxy-5-[1-[4-(4-methylphenoxy)phenoxy]-ethyl]-1,3,4-thiadiazole 0.84 g of 4-(4-methylphenoxy)phenol was dissolved in 5 ml of acetone followed by adding 0.87 g of anhydrous potassium carbonate and 1.0 g of 2-(1-bromoethyl)-5-ethoxy-1,3,4-thiadiazole. The resulting mixture was refluxed with stirring and heating for 2 hours. After cooling, insoluble salts were filtered off, and acetone was distilled off under reduced pressure. The residue was purified by chromatography on silica gel to obtain 1.1 g of the compound No. 10 described in Table 1.

The typical compounds of the invention produced using similar procedures are shown in Table 1. The data on nuclear magnetic resonance spectra were described in accordance with the usual method. The measurements were carried out using tetramethylsilane as an internal standard substance and $CDCl_3$ or $CCl_4$ as a solvent.

| No. | Structural formula | Physical property | Nuclear magnetic resonance spectra (δ, ppm) [Measurement solvent] | Synthesis example No. |
|---|---|---|---|---|
| 1 | (structure) | $n_D^{25.0}$ 1.5882 | 1.46(3H,t), 4.56(2H,q), 5.30(2H,s), 6.8–7.5(9H,m) [CDCl$_3$] | 4 |
| 2 | (structure) | $n_D^{25.0}$ 1.5780 | 1.46(3H,t), 1.73(3H,d), 4.56(2H,q), 5.60(1H,q), 6.8–7.5(9H,m) [CDCl$_3$] | 5 |
| 3 | (structure) | $n_D^{25.0}$ 1.5930 | 1.48(3H,t), 4.55(2H,q), 5.30(2H,s), 6.8–7.4(8H,m) [CDCl$_3$] | 4 |
| 4 | (structure) | mp 67–69° C. | 1.50(3H,t), 4.60(2H,q), 5.33(2H,s), 6.8–7.8(7H,m) [CDCl$_3$] | 4 |

-continued

| No. | Structural formula | Physical property | Nuclear magnetic resonance spectra (δ, ppm) [Measurement solvent] | Synthesis example No. |
|---|---|---|---|---|
| 5 | CF₃-C₆H₄-O-C₆H₄-O-CH(CH₃)-C(=N-N=)S-C(OC₂H₅) | mp 57–58° C. | 1.50(3H,t), 1.80(3H,d), 4.60(2H,q), 5.60(1H,q), 6.8–7.7(8H,m) [CDCl₃] | 2 |
| 6 | CF₃-C₆H₄-O-C₆H₄-O-CH(CH₃)-C(=N-N=)S-C(SCH₃) | $n_D^{25.0}$ 1.5721 | 1.80(3H,d), 2.80(3H,s), 5.76(1H,q), 6.8–7.7(8H,m) [CDCl₃] | 3 |
| 7 | Cl-C₆H₄-O-C₆H₄-O-CH(CH₃)-C(=N-N=)S-C(OC₂H₅) | $n_D^{25.0}$ 1.5859 | 1.43(3H,t), 1.73(3H,d), 4.55(2H,q), 5.55(1H,q), 6.8–7.4(8H,m) [CDCl₃] | 1 |
| 8 | (2-Cl, 4-CF₃)C₆H₃-O-C₆H₄-O-CH(CH₃)-C(=N-N=)S-C(OC₂H₅) | $n_D^{22.0}$ 1.5486 | 1.45(3H,t), 1.75(3H,d), 4.58(2H,q), 5.53(1H,q), 6.7–7.2(5H,m), 7.38(1H,d-d), 7.71(1H,d) [CCl₄] | 5 |
| 9 | (methylenedioxy)C₆H₃-O-C₆H₄-O-CH(CH₃)-C(=N-N=)S-C(OC₂H₅) | $n_D^{22.0}$ 1.5840 | 1.44(3H,t), 1.72(3H,d), 4.54(2H,q), 5.47(1H,q), 5.94(2H,s), 6.3–7.0(7H,m) [CCl₄] | 5 |
| 10 | CH₃-C₆H₄-O-C₆H₄-O-CH(CH₃)-C(=N-N=)S-C(OC₂H₅) | $n_D^{25.0}$ 1.5732 | 1.45(3H,t), 1.73(3H,d), 2.30(3H,s) 4.54(2H,q), 5.47(1H,q), 6.7–7.2(8H,m) [CCl₄] | 5 |
| 11 | (2-CF₃)C₆H₄-O-C₆H₄-O-CH(CH₃)-C(=N-N=)S-C(OC₂H₅) | $n_D^{23.0}$ 1.5435 | 1.47(3H,t), 1.77(3H,d), 4.56(2H,q), 5.53(1H,q), 6.7–7.8(8H,m) [CCl₄] | 5 |
| 12 | (3-CF₃)C₆H₄-O-C₆H₄-O-CH(CH₃)-C(=N-N=)S-C(OC₂H₅) | $n_D^{23.0}$ 1.5409 | 1.45(3H,t), 1.74(3H,d), 4.55(2H,q), 5.51(1H,q), 6.7–7.6(8H,m) [CCl₄] | 5 |
| 13 | (CH₃)₃C-C₆H₄-O-C₆H₄-O-CH(CH₃)-C(=N-N=)S-C(OC₂H₅) | $n_D^{23.0}$ 1.5616 | 1.32(9H,s), 1.47(3H,t), 1.74(3H,d), 4.54(2H,q), 5.47(1H,q), 6.7–7.0(6H,m), 7.25(2H,d), [CCl₄] | 5 |
| 14 | O₂N-C₆H₄-O-C₆H₄-O-CH(CH₃)-C(=N-N=)S-C(OC₂H₅) | mp 70.5–71.5° C. | 1.47(3H,t), 1.79(3H,d), 4.59(2H,q), 5.60(1H,q), 6.8–7.2(6H,m), 8.18(2H,s) [CDCl₃] | 5 |
| 15 | NC-C₆H₄-O-C₆H₄-O-CH(CH₃)-C(=N-N=)S-C(OC₂H₅) | mp 66.5–67.5° C. | 1.47(3H,t), 1.77(3H,d), 4.56(2H,q), 5.53(1H,q), 6.8–7.2(6H,m), 7.55(2H,d-d) [CCl₄] | 5 |

-continued

| No. | Structural formula | Physical property | Nuclear magnetic resonance spectra (δ, ppm) [Measurement solvent] | Synthesis example No. |
|---|---|---|---|---|
| 16 | Cl-, Cl-phenyl-O-phenyl-O-CH(CH₃)-C(=N-N)-S-C(OC₂H₅) | mp 80–81° C. | 1.47(3H,t), 1.76(3H,d), 4.56(2H,q), 5.51(1H,q), 6.7–7.1(6H,m), 7.31(1H,d) [CCl₄] | 5 |
| 17 | CF₃-phenyl-O-phenyl-O-CH(C₂H₅)-C(=N-N)-S-C(OC₂H₅) | $n_D^{20.0}$ 1.5370 | 1.10(3H,t), 1.45(3H,t), 1.9–2.3(2H,m), 1.55(2H,q), 5.35(1H,t), 6.9–7.6(8H,m) [CDCl₃] | 4 |
| 18 | CF₃-phenyl-O-phenyl-O-CH(C₃H₇-n)-C(=N-N)-S-C(OC₂H₅) | $n_D^{20.0}$ 1.5345 | 1.00(3H,t), 1.45(3H,t), 1.3–1.8(2H,m), 1.8–2.2(2H,m), 4.55(2H,q), 5.45(1H,t), 6.9–7.6(8H,m) [CDCl₃] | 4 |
| 19 | CF₃-phenyl-O-phenyl-O-CH₂-C(=N-N)-S-C(OC₂H₅) | mp 96–98° C. | 1.45(3H,t), 4.55(2H,q), 5.30(2H,s), 6.9–7.1(6H,m), 7.57(2H,d) [CDCl₃] | 4 |
| 20 | CF₃-phenyl-O-phenyl-O-CH(CH₃)-C(=N-N)-S-C(OCH₃) | $n_D^{20.5}$ 1.5455 | 1.75(3H,d), 4.20(3H,s), 5.60(1H,q), 6.9–7.7(8H,m) [CDCl₃] | 4 |
| 21 | CF₃-phenyl-O-phenyl-O-CH(CH₃)-C(=N-N)-S-C(OC₃H₇-n) | $n_D^{23.5}$ 1.5355 | 1.03(3H,t), 1.75(3H,d), 1.80(2H,m), 4.50(2H,t), 5.60(1H,q), 6.9–7.5(8H,m) [CDCl₃] | 4 |
| 22 | CF₃-phenyl-O-phenyl-O-CH(CH₃)-C(=N-N)-S-C(OC₃H₇-i) | $n_D^{22.5}$ 1.5357 | 1.50(6H,d), 1.80(3H,d), 5.35(1H,m), 5.60(1H,q), 6.9–7.7(8H,m) [CDCl₃] | 4 |
| 23 | CF₃-phenyl-O-phenyl-O-CH(CH₃)-C(=N-N)-S-C(SC₂H₅) | $n_D^{20.0}$ 1.5682 | 1.50(3H,t), 1.80(3H,d), 3.35(2H,q), 5.77(1H,q), 6.9–7.7(8H,m) [CDCl₃] | 3 |
| 24 | CF₃-phenyl-O-phenyl-O-CH(CH₃)-C(=N-N)-S-C(NHCH₃) | mp 119–120° C. | 1.70(3H,d), 3.05(3H,s), 5.60(1H,q), 6.20(1H,brs), 6.8–7.1(6H,m), 7.55(2H,d) [CDCl₃] | 2 |
| 25 | CF₃-phenyl-O-phenyl-O-CH(CH₃)-C(=N-N)-S-C(N(CH₃)₂) | $n_D^{25.0}$ 1.5310 | 1.75(3H,d), 3.13(6H,s), 5.60(1H,q), 6.85–7.7(8H,m) [CDCl₃] | 2 |
| 26 | CF₃-phenyl-O-phenyl-O-CH(CH₃)-C(=N-N)-S-C(C₃H₇-n) | $n_D^{25.0}$ 1.5372 | 1.05(3H,t), 1.80(3H,d), 1.80(2H,m), 3.10(2H,t), 5.80(1H,q), 6.9–7.1(6H,m), 7.50(2H,d), [CDCl₃] | 2 |
| 27 | phenyl-O-phenyl-O-CH(CH₃)-C(=N-N)-S-C(OC₂H₅) | $n_D^{22}$ 1.5800 | 1.44(3H,t), 1.73(3H,d), 4.56(2H,q), 5.57(1H,q), 6.5–7.5(9H,m) [CCl₄] | 5 |

-continued

| No. | Structural formula | Physical property | Nuclear magnetic resonance spectra (δ, ppm) [Measurement solvent] | Synthesis example No. |
|---|---|---|---|---|
| 28 | CF$_3$—⟨⟩—O—⟨⟩—O—CH(CH$_3$)—C(=N—N=C(S)OC$_2$H$_5$) | $n_D^{55}$ 1.5397 | 1.47(3H,t), 1.74(3H,d), 4.55(2H,q), 5.55(1H,q) 6.5–7.7(8H,m) [CCl$_4$] | 5 |
| 29 | (CF$_3$)⟨⟩—⟨⟩—O—⟨⟩—O—CH(CH$_3$)—C(=N—N=C(S)OC$_2$H$_5$) | $n_D^{25.5}$ 1.5379 | 1.39(3H,t), 1.77(3H,d), 4.56(2H,q), 5.54(1H,q) 6.45–7.6(8H,m) [CCl$_4$] | 5 |
| 30 | CF$_3$—⟨⟩—O—⟨⟩—O—(CH$_2$)$_3$—C(=N—N=C(S)OC$_2$H$_5$) | mp 77.5–79.5° C. | 1.48(3H,t), 2.27(2H,quintet), 3.10(2H,t), 4.06(2H,t), 4.55(2H,q), 6.7–7.1(6H,m), 7.54(2H,d), [CCl$_4$] | 4 |

Next, the preparation examples of the compounds of the invention will be described. The parts and percentages in the following examples are units by weight.

PREPARATION EXAMPLE 1: WETTABLE POWDER 40 parts of the compound No. 5 of the invention in Table 1, 20 parts of Carplex #80 (trade name, manufactured by Shionogi Pharmaceutical Co., Ltd.), 35 parts of N,N Kaolin Clay (trade name, manufactured by Tsuchiya Kaolin Co., Ltd.) and 5 parts of the higher alcohol sulfate-based surfactant Sorpole 8070 (trade name, manufactured by Toho Chemical Co., Ltd.) were compounded and homogeneously mixed and pulverized to obtain a wettable powder containing 40% of the active ingredient.

PREPARATION EXAMPLE 2: DUST 2 parts of the compound No. 6 of the invention in Table 1, 93 parts of NC Clay (trade name, manufactured by Itsushima Kozan) and 5 parts of Carplex #80 (trade name, manufactured by Shionogi Pharmaceutical Co., Ltd.) were homogeneously mixed and pulverized to obtain a dust.

PREPARATION EXAMPLE 3: EMULSION 30 parts of the compound No. 5 of the invention in Table 1 was dissolved in a mixed solvent comprising 30 parts of xylene and 25 parts of dimethylformamide. To the resulting mixture was added 15 parts of the polyoxyethylene-based surfactant Sorpole 3005X (trade name, manufactured by Toho Chemical Co., Ltd.) to obtain an emulsion containing 30% of the active ingredient.

PREPARATION EXAMPLE 4: FLOWABLE AGENT 30 parts of the compound NO. 4 of the invention in Table 1 was thoroughly mixed with and dispersed in premixed 8 parts of ethylene glycol, 5 parts of Sorpole AC3032 (trade name, manufactured by Toho Chemical Co., Ltd.), 0.1 part of xanthane gum and 56.9 parts of water. Hereafter, the mixture in slurry was wet-pulverized using a dinomill (manufactured by Sinmal Enterprises Co., Ltd.) to obtain a stable flowable agent containing 30% of the active ingredient.

TEST EXAMPLE 1: EFFECT ON BROWN PLANTHOPPER (*Nilaparvata lugens*)

The wettable powder containing the compound of the invention prepared in accordance with the prescription of Preparation Example 1 was diluted with water so as to adjust the concentration of the effective ingredient to 1,000 ppm. Five brown planthoppers (*Nilaparvata lugens*) and young rice plants were placed in a glass cylinder (diameter: 3 cm, height: 18 cm), and a cap stuck with a mesh was put on the cylinder. The above water solution was sprayed from the top of the cylinder so that 0.5 ml of the water solution was sprayed per cylinder, and the cylinder was then left in a thermostatic chamber at 25°±1° C. After 24 hours, the numbers of live and dead insects in each cylinder were examined, and the percentage of mortality was calculated by the following equation.

$$\text{Mortality (\%)} = \frac{\text{Number of dead insects}}{\text{Number of dead insects + Number of live insects}} \times 100$$

Incidentally, 20 insects were subjected to each test. The results are shown in Table 2.

TABLE 2

| Effect on brown planthopper (*Nilaparvata lugens*) | | |
|---|---|---|
| Compound No. | Concentration (ppm) | Mortality (%) |
| 2 | 1000 | 90 |
| 4 | 1000 | 95 |
| 5 | 1000 | 100 |
| 9 | 1000 | 100 |
| 12 | 1000 | 100 |
| 13 | 1000 | 80 |
| 16 | 1000 | 95 |
| 20 | 1000 | 100 |
| 24 | 1000 | 90 |
| 27 | 1000 | 100 |
| Control | — | 0 |

TEST EXAMPLE 2: EFFECT ON ADZUKI BEAN WEEVIL

(Callosobruchus maculatus)

1,000 ppm water solution of the compound of the invention was prepared in a similar manner as in Test Example 1. Ten adzuki bean weevils (*Callosobruchus maculatus*) were placed in a glass cylinder (diameter: 3 cm, height: 13 cm), and a cap stuck with a mesh was put on the cylinder. The above water solution was sprayed from the top of the cylinder so that 0.5 ml of the water solution was sprayed per cylinder, and the cylinder was then left in a thermostatic chamber at 25°±1° C. After 24 hours, the numbers of live and dead insects in each cylinder were examined, and the percentage of mortality was calculated in the same manner as in Test Example 1.

Incidentally, 20 insects were subjected to each test. The results are shown in Table 3.

TABLE 3

Effect on adzuki bean weevil (*Callosobruchus maculatus*)

| Compound No. | Concentration (ppm) | Mortality (%) |
|---|---|---|
| 1 | 1000 | 100 |
| 3 | 1000 | 90 |
| 5 | 1000 | 100 |
| 19 | 1000 | 100 |
| 23 | 1000 | 95 |
| 25 | 1000 | 80 |
| 30 | 1000 | 90 |
| Control | — | 0 |

TEST EXAMPLE 3: EFFECT ON TWO-SPOTTED SPIDER MITE

(Tetranychus urticae)

Two female adult two-spotted spider mites (*Tetranychus urticae*) were put onto a leaf disk (diameter: 2 cm) of kidney bean leaf. After allowing to be put onto the leaf disk, the two female adults were made to lay eggs for 20 hours, and the female adults were removed. The wettable powder containing the compound of the invention prepared in accordance with the prescription of Preparation Example 1 wad diluted with water to the prescribed concentration, and the above leaf disk on which the eggs had been laid was dipped in the diluted solution for 5 seconds.

At 10 days after the treatment, the number of unhatched eggs and the life and death of hatched-out larvae were examined, and the effect on eggs and hatched-out larvae was determined by the following method.

Effect on eggs and hatched-out out larvae (%) =

$$\frac{\text{Number of unhatched eggs + Number of dead hatched-out larvae}}{\text{Number of eggs treated}} \times 100$$

The results are shown in Table 4.

TABLE 4

Effect on two-spotted spider mite (*Tetranychus urticae*)

| Compound No. | Concentration (ppm) | Effect on eggs and hatched-out larvae (%) |
|---|---|---|
| 1 | 1000 | 100 |
| 2 | 1000 | 100 |
| 3 | 1000 | 100 |
| 4 | 1000 | 100 |
| 5 | 1000 | 100 |
|   | 500  | 100 |
| 6 | 1000 | 100 |
|   | 500  | 100 |
| 7 | 1000 | 100 |
| 8 | 1000 | 100 |
| 10 | 1000 | 90 |
| 15 | 1000 | 100 |
|    | 500  | 90 |
| 20 | 1000 | 100 |
| 21 | 1000 | 100 |
| 22 | 1000 | 100 |
|    | 500  | 100 |
| 26 | 1000 | 90 |
| 27 | 1000 | 80 |
| 28 | 1000 | 85 |
| 29 | 1000 | 75 |
| 30 | 1000 | 75 |

What is claimed is:

1. A thiadiazole derivative of the general formula

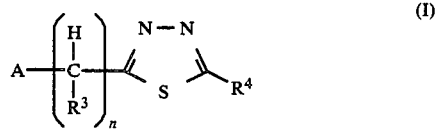

wherein A represents a group of the formula

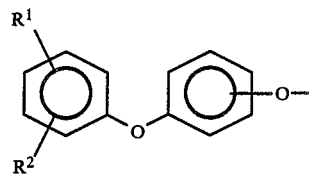

$R^1$ and $R^2$ independently represent a hydrogen atom, a halogen atom, a lower alkyl group, a trifluoromethyl group, a cyano group or a nitro group or jointly represent a methylenedioxy group, $R^3$ represents a hydrogen atom or a lower alkyl group, $R^4$ represents a lower alkyl group, a lower alkoxy group, a lower alkylthio group, a monoalkylamino group having a lower alkyl group or a dialkylamino group having lower alkyl group, and n is an integer of from 1 through 3.

2. A thiadiazole derivative according to claim 1, wherein in the general formula (I), A represents a group of the formula

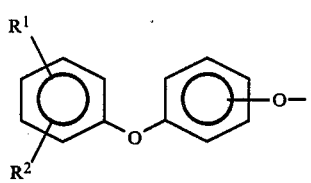

$R^1$ and $R^2$ independently represent a hydrogen atom, a halogen atom, a $C_1$ to $C_4$ lower alkyl group, a trifluoromethyl group, a cyano group or a nitro group or jointly represent a methylenedioxy group, $R^3$ represents a hydrogen atom or a $C_1$ to $C_4$ lower alkyl group, $R^4$ represents a $C_1$ to $C_4$ lower alkyl group, a $C_1$ to $C_4$ lower alkoxy group, a $C_1$ to $C_4$ lower alkylthio group, a monoalkylamino group having a $C_1$ to $C_4$ alkyl group or a dialkylamino group having $C_1$ to $C_4$ alkyl group, and n is an integer of from 1 through 3.

3. A thiadiazole derivative according to claim 1, wherein in the general formula (I), A represents a group of the formula

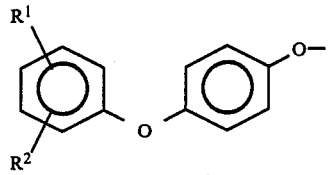

$R^1$ and $R^2$ independently represent a hydrogen atom, a halogen atom, a $C_1$ to $C_4$ lower alkyl group, a trifluoromethyl group or a cyano group or jointly represent a methylenedioxy group, $R^3$ represents a hydrogen atom or a $C_1$ to $C_4$ lower alkyl group, $R^4$ represents a $C_1$ to $C_3$ lower alkyl group, a $C_1$ to $C_4$ lower alkoxy group, a $C_1$ to $C_3$ lower alkylthio group, a monoalkylamino group having a $C_1$ to $C_2$ alkyl group or a dialkylamino group having $C_1$ to $C_2$ alkyl group, and n is an integer of from 1 through 3.

4. A thiadiazole derivative according to claim 1, wherein in the general formula (I), A represents a group of the formula

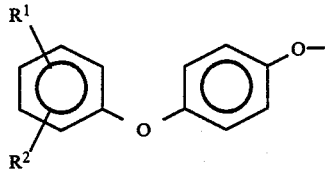

$R^1$ and $R^2$ independently represent a hydrogen atom, a halogen atom, a trifluoromethyl group or a cyano group, $R^3$ represents a $C_1$ to $C_3$ lower alkyl group, $R^4$ represents a $C_1$ to $C_3$ lower alkoxy group or a $C_1$ to $C_3$ lower alkylthio group, and n is 1.

5. A thiadiazole derivative according to claim 1, wherein in the general formula (I), A represents a group of the formula

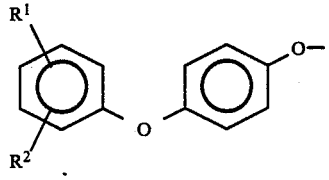

$R^1$ and $R^2$ independently represent a hydrogen atom, a chlorine atom, a bromine atom, a trifluoromethyl group or a cyano group, $R^3$ represents a methyl group, $R^4$ represents a $C_1$ to $C_3$ lower alkoxy group, and n is 1.

6. A thiadiazole derivative according to claims 3 to 5, wherein either of $R^1$ and $R^2$ is a halogen atom, a trifluoromethyl group or a cyano group by which the 4-position is substituted.

7. A thiadiazole derivative according to claim 1, wherein in the general formula (I), A represents a group of the formula

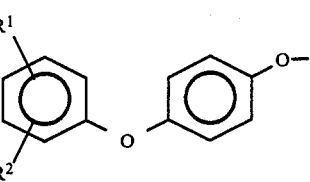

$R^1$ represents a hydrogen atom, $R^2$ represents a trifluoromethyl group, $R^3$ represents a methyl group, $R^4$ represents a $C_1$ to $C_3$ lower alkoxy group, and n is 1.

8. An insecticidal and miticidal composition comprising a thiadiazole derivative of the following general formula (I), as an active ingredient and an appropriate adjuvants:

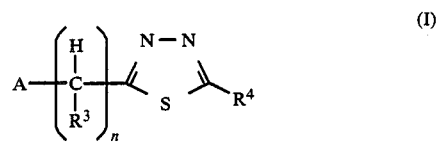

wherein A represents a group of the formula

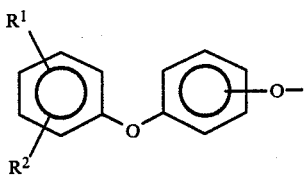

$R^1$ and $R^2$ independently represent a hydrogen atom, a halogen atom, a lower alkyl group, a trifluoromethyl group, a cyano group or a nitro group or jointly represent a methylenedioxy group, $R^3$ represents a hydrogen atom or a lower alkyl group, $R^4$ represents a lower alkyl group, a lower alkoxy group, a lower alkylthio group, a monoalkylamino group having a lower alkyl group or a dialkylamino group having lower alkyl group, and n is an integer of from 1 through 3.

9. An insecticidal and miticidal composition according to claim 8, wherein in the general formula (I), A represents a group of the formula

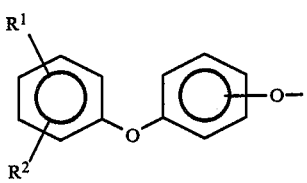

$R^1$ and $R^2$ independently represent a hydrogen atom, a halogen atom, a $C_1$ to $C_4$ lower alkyl group, a trifluoromethyl group, a cyano group or a nitro group or jointly represent a methylenedioxy group, $R^3$ represents a hydrogen atom or a $C_1$ to $C_4$ lower alkyl group, $R^4$ represents a $C_1$ to $C_4$ lower alkyl group, a $C_1$ to $C_4$ lower alkoxy group, a $C_1$ to $C_4$ lower alkylthio group, a monoalkylamino group having a $C_1$ to $C_4$ alkyl group or a dialkylamino group having $C_1$ to $C_4$ alkyl group, and n is an integer of from 1 through 3.

10. An insecticidal and miticidal composition according to claim 8, wherein in the general formula (I), A represents a group of the formula

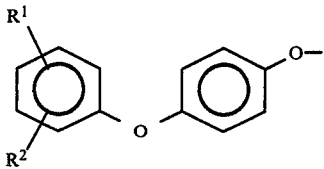

$R^1$ and $R^2$ independently represent a hydrogen atom, a halogen atom, a $C_1$ to $C_4$ lower alkyl group, a trifluoromethyl group or a cyano group or jointly represent a methylenedioxy group, $R^3$ represents a hydrogen atom or a $C_1$ to $C_4$ lower alkyl group, $R^4$ represents a $C_1$ to $C_3$ lower alkyl group, a $C_1$ to $C_4$ lower alkoxy group, a $C_1$ to $C_3$ lower alkylthio group, a monoalkylamino group having a $C_1$ to $C_2$ alkyl group or a dialkylamino group having $C_1$ to $C_2$ alkyl group, and n is an integer of from 1 through 3.

11. An insecticidal and miticidal composition according to claim 8, wherein in the general formula (I), A represents a group of the formula

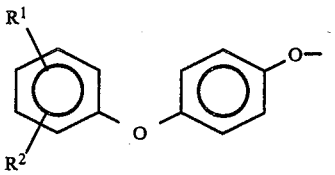

$R^1$ and $R^2$ independently represent a hydrogen atom, a halogen atom, a trifluoromethyl group or a cyano group, $R^3$ represents a $C_1$ to $C_3$ lower alkyl group, $R^4$ represents a $C_1$ to $C_3$ lower alkoxy group or a $C_1$ to $C_3$ lower alkylthio group, and n is 1.

12. An insecticidal and miticidal composition according to claim 8, wherein in the general formula (I), A represents a group of the formula

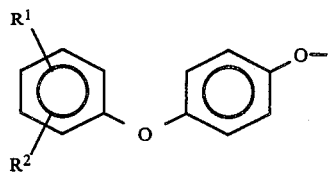

$R^1$ and $R^2$ independently represents a hydrogen atom, a chlorine atom, a bromine atom, a trifluoromethyl group or a cyano group, $R^3$ represents a methyl group, $R^4$ represents a $C_1$ to $C_3$ lower alkoxy group, and n is 1.

13. An insecticidal and miticidal composition according to claims 10 to 12, wherein either of $R^1$ and $R^2$ is a halogen atom, a trifluoromethyl group or a cyano group by which the 4-position is substituted.

14. An insecticidal and miticidal composition according to claim 8, wherein in the general formula (I), A represents a group of the formula

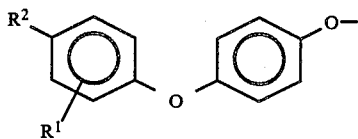

$R^1$ represents a hydrogen atom, $R^2$ represents a trifluoromethyl group, $R^3$ represents a methyl group, $R^4$ represents a $C_1$ to $C_3$ lower alkoxy group, and n is 1.

* * * * *